United States Patent
Brown et al.

(10) Patent No.: US 12,350,177 B2
(45) Date of Patent: Jul. 8, 2025

(54) MINIMALLY INVASIVE IMPLANTABLE DEVICES

(71) Applicant: Cook Medical Technologies LLC, Bloomington, IN (US)

(72) Inventors: Elizabeth M. Brown, Bloomington, IN (US); Donald R. Sandmore, Ellettsville, IN (US); Kathryn R. Hardert, Bloomington, IN (US); Erin Roberts, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 88 days.

(21) Appl. No.: 17/701,311

(22) Filed: Mar. 22, 2022

(65) Prior Publication Data
US 2022/0313457 A1 Oct. 6, 2022

Related U.S. Application Data

(60) Provisional application No. 63/171,470, filed on Apr. 6, 2021.

(51) Int. Cl.
*A61F 2/04* (2013.01)
*A61F 2/00* (2006.01)
*A61F 2/848* (2013.01)
*A61F 2/90* (2013.01)

(52) U.S. Cl.
CPC ............ *A61F 2/848* (2013.01); *A61F 2/0077* (2013.01); *A61F 2/90* (2013.01); *A61F 2002/047* (2013.01); *A61F 2220/0008* (2013.01); *A61F 2220/0075* (2013.01); *A61F 2250/0039* (2013.01)

(58) Field of Classification Search
None
See application file for complete search history.

(56) References Cited

U.S. PATENT DOCUMENTS

| | | | |
|---|---|---|---|
| 5,064,435 A * | 11/1991 | Porter | A61F 2/90 606/198 |
| 6,770,101 B2 | 8/2004 | Desmond | |
| 8,486,154 B2 | 7/2013 | Cerebel | |

(Continued)

FOREIGN PATENT DOCUMENTS

CN 106473848 A 3/2017

OTHER PUBLICATIONS https://www.allium-medical.com/products/triangular-prostatic-stents/, ,—TPS—Triangular Prostatic Stents, downloaded Nov. 2, 2020, 3pp.

*Primary Examiner* — Leslie A Lopez
(74) *Attorney, Agent, or Firm* — Crowell & Moring LLP

(57) ABSTRACT

A minimally invasive implantable device has a generally cylindrical device body that includes: a first end having a first element; a second end having a second element; a wall disposed between the first end and the second end, and having an inner surface and an outer surface, wherein the inner surface defines a lumen extending between the first end and the second end; and at least one protruding element protruding from the outer surface, wherein an outermost diameter of the first element and an outermost diameter of the second element is larger than a diameter of the outer surface of the wall, and the at least one protruding element does not protrude beyond the outermost diameter of the first element or the outermost diameter of the second element.

8 Claims, 2 Drawing Sheets

(56) References Cited

U.S. PATENT DOCUMENTS

| | | |
|---|---|---|
| 9,232,992 B2 | 1/2016 | Heidner |
| 9,333,102 B2 | 5/2016 | Yachia |
| 10,183,442 B1 | 1/2019 | Miller |
| 10,758,380 B2 | 9/2020 | Bluecher |
| 2003/0135268 A1 | 7/2003 | Desai |
| 2004/0073155 A1* | 4/2004 | Laufer .................. A61B 8/12 623/23.65 |
| 2008/0221659 A1* | 9/2008 | Hartley .................. A61F 2/07 623/1.13 |
| 2012/0059387 A1 | 3/2012 | Schanz |
| 2014/0114408 A1* | 4/2014 | Dwork ................ A61F 2/2433 623/2.18 |
| 2020/0214858 A1 | 7/2020 | Gilmartin |
| 2020/0281710 A1 | 9/2020 | Shadduck |

\* cited by examiner

MINIMALLY INVASIVE IMPLANTABLE DEVICES

CROSS-REFERENCE TO RELATED APPLICATIONS

This application claims priority from U.S. Provisional Application No. 63/171,470, filed Apr. 6, 2021, the entirety of which is hereby fully incorporated by reference herein.

TECHNICAL FIELD

The present disclosure relates to devices for treating benign prostatic hyperplasia (BPH) and associated lower urinary tract symptoms infections (LUTS).

BACKGROUND

The statements in this section merely provide background information related to the present disclosure and may not constitute prior art.

Benign prostatic hyperplasia (BPH) is a urological disease in which the prostate gland enlarges and constricts the urethra. The diagnosis and treatment of BPH currently affects approximately 90 million individuals in the male population over 50 years of age, worldwide, and many more are likely affected but not being treated. BPH may manifest clinically in storage and voiding symptoms collectively termed lower urinary tract symptoms (LUTS). Although LUTS secondary to BPH are not often life-threatening, the impact on quality of life can be significant.

Pharmacologic therapy is the prevalent first-line approach. Exemplary drugs approved by the U.S. FDA include Finasteride (Proscar®), dutasteride (Avodart®), terazosin (Hytrin®), doxazosin (Cardura®), tamsulosin (Flomax®), and alfuzosin (Uroxatral®). These drugs relax the smooth muscle of the prostate and bladder neck to improve urine flow and to reduce bladder outlet obstruction.

Alternatively, various surgical treatments including open prostatectomy to completely or partially remove the gland, transurethral resection of the prostate (TURP) may be employed. However, surgical treatment is an extremely invasive procedure, which can be debilitating and painful to the patient. Various undesirable side effects of such invasive procedures include impotence, incontinence, and bleeding, and infection may result.

Since 2016, several novel, minimally invasive surgical therapies (MISTs) have been successfully introduced, driven by a large population of men who desire a definitive treatment with reduced surgical risk, lesser side effects, and faster recovery than surgery. Such MISTs include transurethral microwave thermotherapy (TUMT), which uses microwaves to heat and destroy portions of prostate tissue, transurethral needle ablation (TUNA), which employs low-level radio-frequency energy delivered through twin needles to burn away selected regions of the enlarged prostate, and water-induced thermotherapy, which uses heated water to destroy portions of prostate tissue. The marked adoption of MISTs and incorporation into the clinical guidelines represents a notable shift in the management of BPH. In accordance with various techniques, global sales of devices to treat symptomatic BPH totaled $421 million in 2016.

Mechanical MISTs, in particular, represent an attractive option for treating LUTS secondary to BPH without cutting, ablating, heating, or removing prostatic tissue. Furthermore, implantable mechanical MISTs can be placed relatively quickly, in the outpatient setting, and with low risk of sexual side effects, making them an attractive option to patients and providers. However, research has shown that certain implantable devices migrate and/or rotate within the patient's body after implantation, which is not desirable.

BRIEF SUMMARY

The present disclosure provides minimally invasive implantable devices for treating benign prostatic hyperplasia (BPH) and associated lower urinary tract symptoms infections (LUTS).

The present disclosure provides minimally invasive implantable devices with increased contact area to inhibit migration or rotation within the patient's body after implantation while allowing easy removal when desired to avoid effects such as encrustation in the implanted region, which may be observed when implanted for a long-term.

In one form, a minimally invasive implantable device has a device body including: a first end having a first element; a second end having a second element; a generally cylindrical wall disposed between the first end and the second end, and having an inner surface and an outer surface, wherein the inner surface defines a lumen extending between the first end and the second end; and at least one protruding element protruding from the outer surface, wherein an outermost diameter of the first element and an outermost diameter of the second element both are larger than a diameter of the outer surface of the wall, and the at least one protruding element does not protrude beyond the outermost diameter of the first element or the outermost diameter of the second element.

In one form, the at least one protruding element may be configured in a screw thread pattern that appears as alternating ribs when viewed from a side.

In one form, the at least one protruding element may be comprised of a plurality of discrete ribs.

In one form, the at least one protruding element may be comprised of a first rib with a right-handed screw thread pattern from the second end; and a second rib with a left-handed screw thread pattern from the first end.

In one form, the at least one protruding element may be comprised of a plurality of discrete protrusions protruding generally perpendicularly to the outer surface.

In one form, the at least one protruding element may be comprised of a plurality of protrusions pointing at an angle toward a center of the device or away from the center of the device toward either the first end or the second end.

In one form, the minimally invasive implantable device may be made of nitinol. Alternatively, the minimally invasive implantable device may be made of stainless steel, silicone, or other moldable plastics.

In one form, the minimally invasive implantable device may be further comprised of a removal element attached to the second end and configured to enable removal from a patient in vivo.

In one form, the first element, the second element, and the at least one protruding element are formed integrally with the device body or are separately attached to the device body.

In another form, a minimally invasive implantable device has a device body including: a first end portion having a first end; a second end portion having a second end; a mid-body portion having a mid-body first end and a mid-body second end, wherein a diameter of the mid-body first end is smaller than a diameter of the first end and a diameter of the mid-body second end is smaller than a diameter of the second end; a first wall disposed between the first end and the mid-body first end, configured in a funnel-shape, and having a first inner surface; a second wall disposed between the mid-body first end and the mid-body second end, and having a second inner surface; and a third wall disposed between the mid-body second end and the second end, configured in the funnel-shape, and having a third inner surface, wherein the first inner surface, the second inner surface, and the third inner surface define a continuous lumen extending between the first end and the second end.

In another form, the mid-body portion may be generally cylindrical.

In another form, the first wall, the second wall, and the third wall are integrally formed or are separately attached to each other.

In another form, the mid-body portion may be comprised of at least one mid-body unit, wherein each mid-body unit of the at least one mid-body unit includes: a mid-end having a diameter that is larger than the diameter of the mid-body first end or the diameter of the mid-body second end; a first unit portion configured in the funnel shape and having a first mid-body inner surface; and a second unit portion configured in the funnel shape and having a second mid-body inner surface, wherein a first end of the first unit portion and a first end of the second unit portion together form the mid-end and the first mid-body inner surface and the second mid-body inner surface form the inner surface of the second wall.

In another form, the at least one mid-body unit may comprise a plurality of mid-body units arranged in series.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

In order that the disclosure may be well understood, there will now be described various forms thereof, given by way of example, reference being made to the accompanying drawings, in which.

Figure 1A:
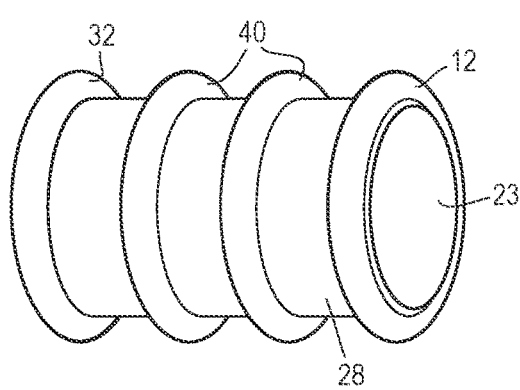
FIGS. 1A and 1B show an exemplary minimally invasive implantable device according to one form of the present disclosure in a perspective view and in a cross-sectional view, respectively.

The drawings described herein are for illustration purposes only and are not intended to limit the scope of the present disclosure in any way.

DETAILED DESCRIPTION

Various aspects are described below with reference to the drawings in which like elements generally are identified by like numerals. The relationship and functioning of the various elements of the aspects may better be understood by reference to the following detailed description. However, aspects are not limited to those illustrated in the drawings or explicitly described below. It also should be understood that the drawings are not necessarily to scale, and in certain instances details may have been omitted that are not necessary for an understanding of aspects disclosed herein, such as conventional material, construction, and assembly.

The terms "proximal" and "distal" are used herein to refer to the relative positions of the components of an exemplary medical device. When used herein, "proximal" refers to a position relatively closer to the exterior of the body or closer to a medical professional using the medical device. In contrast, "distal" refers to a position relatively further away from the medical professional using the medical device, or closer to the interior of the body. Relative terminology and broader terms such as "generally," "about," "substantially," and the like will be understood by those of ordinary skill in the art as providing clear and definite scope of disclosure and/or claiming. For example, the term "generally perpendicular" will be understood as not requiring exactly 90.00 degrees, but rather including that and functional equivalents within normal manufacturing tolerances and ranges understood by those of skilled in the art to be functional and acceptable.

For the sake of clarity of the present disclosure, the dimensions of structures are depicted as being larger than the actual sizes thereof. It will be understood that, although terms such as "first", "second", etc., may be used herein to describe various elements, these elements are not to be limited by these terms. These terms are only used to distinguish one element from another element. For instance, a "first" element discussed below could be termed a "second" element without departing from the scope of the present disclosure. Similarly, the "second" element could also be termed a "first" element. As used herein, the singular forms are intended to include the plural forms as well, unless the context clearly indicates otherwise.

It will be further understood that the terms "comprise", "include", "have", etc., when used in this specification, specify the presence of stated features, integers, steps, operations, elements, components, or combinations thereof, but do not preclude the presence or addition of one or more other features, integers, steps, operations, elements, components, or combinations thereof. Also, it will be understood that when an element is referred to as being "on" another element, it can be directly on the other element, or intervening elements may be present therebetween.

Figure 1B:
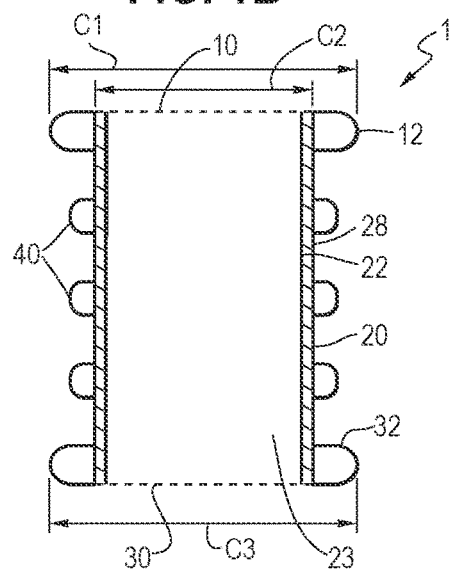

FIGS. 1A and 1B show an exemplary minimally invasive implantable device according to one form of the present disclosure. Minimally invasive implantable devices according to the present disclosure have a generally cylindrical shape to facilitate easy removal.

In one form, the minimally invasive implantable device has a generally cylindrical device body 1 including: a proximal end 10 having a first element 12; a distal end 30 having a second element 32; a wall 20 disposed between the proximal end 10 and the distal end 30, and having an inner surface 22 and an outer surface 28, wherein the inner surface 22 defines a lumen 23 extending between the proximal end 10 and the distal end 30; and at least one protruding element 40 protruding from the outer surface 28, where an outermost diameter c1 of the first element 12 and an outermost diameter c3 of the second element 32 is larger than a diameter c2 of the outer surface 28 of the wall 20, and the at least one protruding element 40 does not protrude beyond the outermost diameter c1 of the first element 12 or the outermost diameter c3 of the second element 32.

Figure 2A:
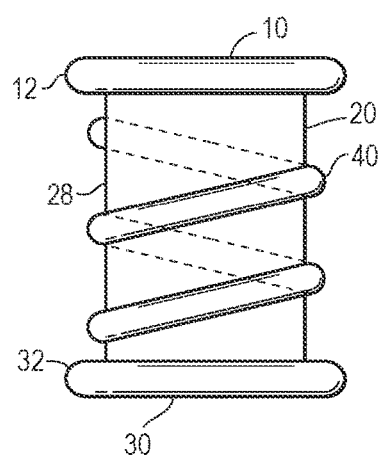
FIGS. 2A to 2E show the minimally invasive implantable devices according to one form of the present disclosure having various configurations of at least one protruding element.
Figure 2B:
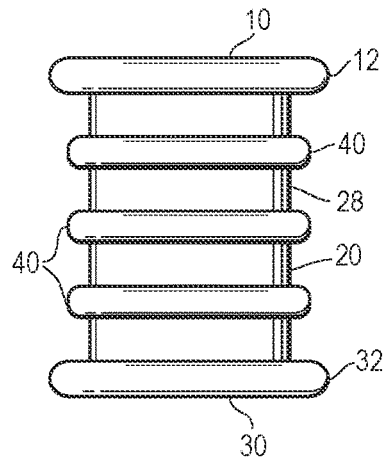
Figure 2C:
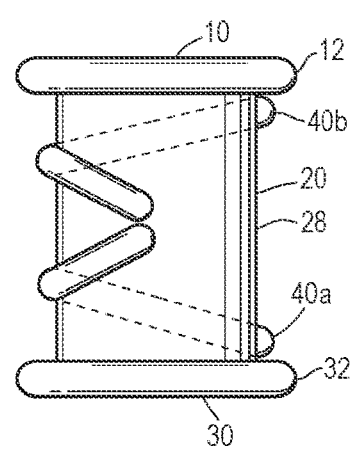

FIGS. 2A to 2E show the minimally invasive implantable devices according to one form of the present disclosure having various configurations of at least one protruding element that protrudes from the outer surface of the device body. Specifically, as shown in FIG. 2A, the at least one protruding element 40 may be configured in a helical (e.g., screw thread-like) pattern that appears as alternating ribs when viewed from a side. Alternatively, as shown in FIG. 2C, the at least one protruding element 40 may be formed of a first rib 40a with a left-handed screw thread pattern from the distal end 30 and a second rib 40b with a left-handed screw thread pattern from the proximal end 10. The direction of the screw pattern may be opposite, in that the at least one protruding element 40 may be formed of a first rib with a right-handed screw thread pattern from the distal end 30 and a second rib with a right-handed screw thread pattern from the proximal end 10.

Figure 2D:
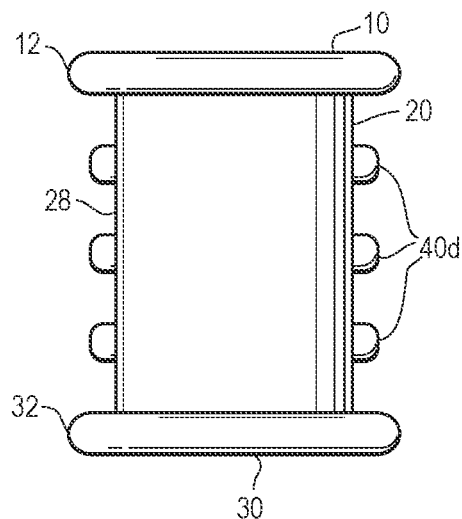
Figure 2E:
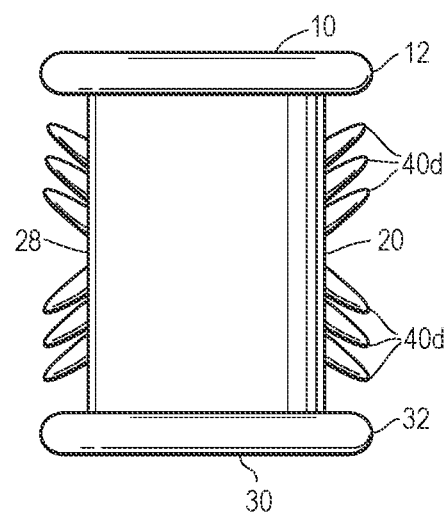

It should be appreciated that such helical pattern(s) may go partially or entirely around the circumference of the wall 20. As another alternative configuration, as shown in FIG. 2B, the at least one protruding element 40 may be comprised of a plurality of discrete ribs. As another alternative configuration, the at least one protruding element 40 may be comprised of a plurality of discrete protrusions 40d. The plurality of discrete protrusions 40d may protrude at an angle generally perpendicular to the outer surface 28, as shown in FIG. 2D, or at an angle pointing away from a center of the device toward either the proximal end 10 or the distal end 30, as shown in FIG. 2E. In some forms, the at least one protruding element 40 may have blunted end(s) to decrease risk of causing pain to the patient when implanted.

Various configurations of the at least one protruding element 40, the first element 12, and the second element 32 are intended to increase the contact area of the device with the body, thereby inhibiting migration or rotation of the device within the patient's body after implantation. Furthermore, the first element 12 and the second element 32 with larger diameters are to provide more opening of the urethra at these areas to ensure adequate reduction in LUTS symptoms. The first element 12 may extend to outside the openings of urethra on the distal side (i.e. in a direction toward bladder) to function as bumpers inhibiting migration within the body. Such configuration inhibits migration and/or rotation within the body after implantation while improving the flow by increasing the contact area around the middle of the device body. Furthermore, such configuration allows the device to stay within the patient body while allowing easy removal from body when desired because the device is not anchored to the tissues.

In one form, the first element 12, the second element 32, and the at least one protruding element 40 may be formed integrally with the device body or may be separately attached to the body. When separately attached, any means of attachment known to a person of ordinary skill in the art, including welding, adhesives, etc., may be used.

Figure 3A:
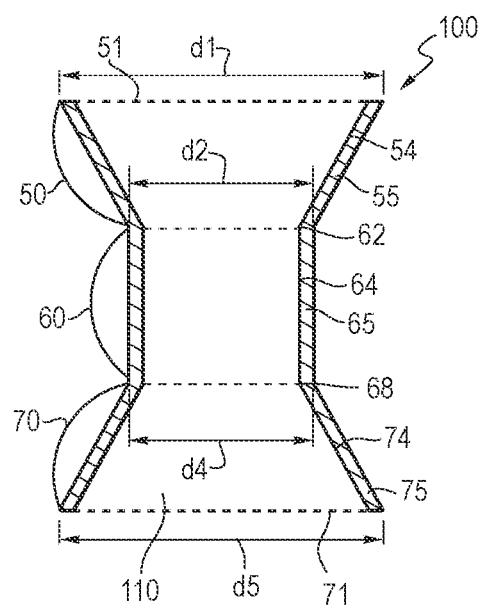
FIGS. 3A and 3B show the minimally invasive implantable devices according to another form of the present disclosure having ends with larger diameters.
Figure 3B:
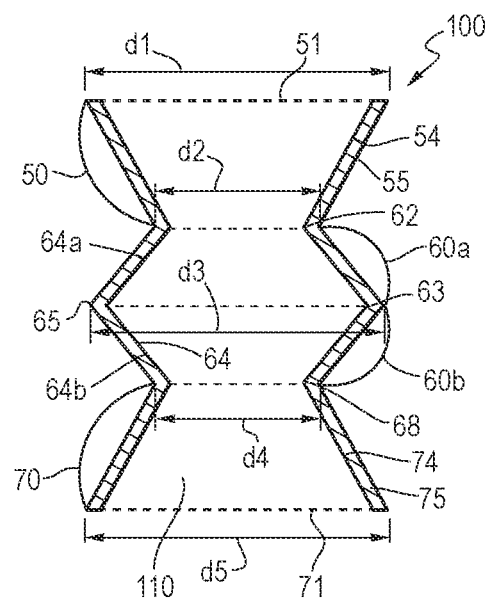

FIGS. 3A and 3B show other forms of minimally invasive implantable devices according to the present disclosure, having varying diameters along the length of the device body.

In another form, a minimally invasive implantable device 100 has a generally cylindrical device body including: a proximal end portion 50 having a proximal end 51; a distal end portion 70 having a distal end 71; a mid-body portion 60 having a mid-body proximal end 62 and a mid-body distal end 68, wherein a diameter d2 of the mid-body proximal end 62 is smaller than a diameter d1 of the proximal end 51 and a diameter d4 of the mid-body distal end 68 is smaller than a diameter d5 of the distal end 71; a first wall 55 disposed between the proximal end 51 and the mid-body proximal end 62, configured in a funnel-shape, and having a first inner surface 54; a second wall 65 disposed between the mid-body proximal end 62 and the mid-body distal end 68, and having a second inner surface 64; and a third wall 75 disposed between the mid-body distal end 68 and the distal end 71, configured in the funnel-shape, and having a third inner surface 74, wherein the first inner surface 54, the second inner surface 64, and the third inner surface 74 define a continuous lumen 110 extending between the proximal end 51 and the distal end 71.

The first wall 55, the second wall 65, and the third wall 75 may be formed of a hoop or ring connected by struts.

The mid-body portion 60 may be generally cylindrical.

Alternatively, the mid-body portion 60 may be comprised of at least one mid-body unit. Each mid-body unit would include a mid-end 63 having a diameter d3 that is larger than the diameter d2 of the mid-body proximal end 62 and/or the diameter d4 of the mid-body distal end 68; a first unit portion 60a configured in the funnel shape and having a first mid-body inner surface 64a; and a second unit portion 60b configured in the funnel shape, and having a second mid-body inner surface 64b, wherein the first mid-body inner surface 64a and the second mid-body inner surface 64b form the second inner surface 64 of the second wall 65.

Here, an end of the first unit portion 60a and an end of the second unit portion 60b together form the mid-end 63 so that each mid-body unit has an enlarged middle portion.

The mid-body portion 60 may include a plurality of mid-body units described above arranged in series, such that the mid-body portion 60 would be configured in an accordion shape when viewed from a side.

In another form, the diameter d3 of the mid-end 63 may not be larger than the diameter d1 of the proximal end 51 or the diameter d5 of the distal end 71. Similarly to the one form discussed above, such configuration with larger diameters at the proximal and distal ends 51 and 71 inhibits migration and/or rotation within the body after implantation while improving the flow by increasing the contact area around the middle of the device body. Portions with larger diameters may extend outside the openings of urethra on the distal side (i.e. in a direction toward bladder) to function as bumpers inhibiting migration within the body. Furthermore, such configuration allows the device to stay within the patient body while allowing easy removal from the body when desired because the device is not anchored to the tissues.

In another form, the proximal end portion 50, the distal end portion 70, and the mid-body portion 60 may be integrally formed or may be separately attached to each other. When separately attached, any means of attachment known to a person of ordinary skill in the art, including welding, adhesives, etc., may be used.

According to the present disclosure, the minimally invasive implantable device may be made of nitinol, stainless steel, silicone, moldable plastics, or any other material with suitable properties that may be deemed suitable by a person of ordinary skill in the art. Examples of moldable plastics may include polyethylene and polyurethane. It is preferable that the device is made of a material that can conform to the patients' anatomy, yet offer sufficient strength to resist collapse or migration within the patient's body. Such configuration may enhance the ability of fluid to flow more readily through the device lumen. In some embodiments, the minimally invasive implantable device may be made of a combination of materials (e.g., layers of different materials, the ends being one kind of material and the middle being a different material, or the ends and the middle part each being any combination of materials, as desired and/or needed).

According to the present disclosure, the minimally invasive implantable device may further include a removal element (not shown) configured to enable removal from a patient in vivo at anywhere of the device (e.g., at the distal end, the proximal end, or anywhere (e.g., the center) between the proximal end and the distal end of the device). The removal element may be a hole or additional structural element (e.g., a ring) attached by any means, including welding, adhesives, etc., known to a person of ordinary skill in the art. The removal element may further facilitate easy removal from the patient's body when desired.

A person of ordinary skill in the art will appreciate that embodiments not expressly illustrated herein may be practiced within the scope of the present application, including that features described herein for different embodiments may be combined with each other and/or with currently-known or future-developed technologies while remaining within the scope of the present application. In particular, those of skill in the art will appreciate that the different configurations of protruding elements 40 in each different embodiment of each different drawing figure may be used together with and/or instead of any other protruding element configurations. By way of non-limiting example, the protruding features shown and described in FIG. 2D could be used in combination with those in FIG. 2A on different portions of a device. This also includes that any one or more of those protruding feature embodiments could be used together with/on the varied-diameter embodiments of FIGS. 3A and 3B. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A minimally invasive implantable medical device for treating benign prostatic hyperplasia (BPH) and associated lower urinary tract symptoms (LUTS), comprising:
    a first end portion having a first end;
    a second end portion having a second end;
    a mid-body portion having a mid-body first end and a mid-body second end, wherein a diameter of the mid-body first end is smaller than a diameter of the first end and a diameter of the mid-body second end is smaller than a diameter of the second end;
    a first wall disposed between the first end and the mid-body first end, configured in a funnel-shape extending from the first end to the mid-body first end, and having a first inner surface;
    a second wall disposed between the mid-body first end and the mid-body second end, and having a second inner surface; and
    a third wall disposed between the mid-body second end and the second end, configured in the funnel-shape, and having a third inner surface,
    wherein the first inner surface, the second inner surface, and the third inner surface define a continuous lumen extending between the first end and the second end, wherein the mid-body portion includes a mid-body unit, wherein the mid-body unit includes a mid-end having a diameter that is larger than the diameter of the mid-body first end or the diameter of the mid-body second end, and wherein there is a first taper extending from the mid-body first end to the mid-end and a second taper extending from the mid-end to the mid-body second end.

2. The minimally invasive implantable medical device of claim 1, wherein the first wall, the second wall, and the third wall are integrally formed or are separately attached to each other.

3. The minimally invasive implantable medical device of claim 1, wherein the mid-body unit includes:
    a first unit portion configured in a first funnel shape, and having a first mid-body inner surface; and
    a second unit portion configured in a second funnel shape, and having a second mid-body inner surface,
    wherein a first end of the first unit portion and a first end of the second unit portion together form the mid-end, and the first mid-body inner surface and the second mid-body inner surface form at least a portion of the second inner surface of the second wall.

4. The minimally invasive implantable medical device of claim 1, wherein the diameter of the mid-end is not larger than the diameter of the first end.

5. The minimally invasive implantable medical device of claim 1, wherein the diameter of the mid-end is not larger than the diameter of the second end.

6. The minimally invasive implantable medical device of claim 1, wherein the first end portion and the second end portion are made of a first material, wherein the mid-body portion is made of a second material, and wherein the first and the second materials are different.

7. The minimally invasive implantable medical device of claim 1, further comprising a removal component configured to enable removal of the minimally invasive implantable medical device from a patient's body.

8. A minimally invasive implantable medical device for treating benign prostatic hyperplasia (BPH) and associated lower urinary tract symptoms (LUTS), comprising:
    a first terminal end;
    a second terminal end; and
    a wall disposed between the first terminal end and the second terminal end, and having an inner surface and an outer surface, wherein the inner surface defines a lumen extending between the first terminal end and the second terminal end,
    wherein the wall has a mid-body portion having a mid-body first end and a mid-body second end, wherein a diameter of the mid-body first end is smaller than a diameter of the first terminal end and a diameter of the mid-body second end is smaller than a diameter of the second terminal end, and
    wherein the mid-body portion includes a mid-end having a diameter that is at least equal to the diameter of the first terminal end or the diameter of the second terminal end.

* * * * *